(12) United States Patent
Su et al.

(10) Patent No.: US 9,968,646 B2
(45) Date of Patent: May 15, 2018

(54) METHOD FOR TREATMENT OF PROSTATIC HYPERPLASIA AND/OR AMELIORATING URINARY DISTURBANCE WITH BANANA FLOWER EXTRACT

(71) Applicant: TCI Co., Ltd., Taipei (TW)

(72) Inventors: Hsiang-Ling Su, Taipei (TW); Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days. days.

(21) Appl. No.: 14/861,338

(22) Filed: Sep. 22, 2015

(65) Prior Publication Data

US 2016/0082067 A1  Mar. 24, 2016

(30) Foreign Application Priority Data

Sep. 22, 2014  (TW) ............................. 103132577 A
Aug. 27, 2015  (TW) ............................. 104128175 A

(51) Int. Cl.
| | |
|---|---|
| *A61K 36/88* | (2006.01) |
| *A61P 13/08* | (2006.01) |
| *A61K 9/48* | (2006.01) |
| *A23L 33/105* | (2016.01) |

(52) U.S. Cl.
CPC ............ *A61K 36/88* (2013.01); *A23L 33/105* (2016.08); *A61K 9/4816* (2013.01); *A61P 13/08* (2018.01); *A23V 2002/00* (2013.01)

(58) Field of Classification Search
None
See application file for complete search history.

(56) References Cited

U.S. PATENT DOCUMENTS

2009/0324750 A1* 12/2009 Lee ........................ A61K 31/35
                                                              424/725
2010/0316748 A1* 12/2010 Fouche .................. A61K 36/48
                                                              424/757

OTHER PUBLICATIONS

Dhanabal, S. P., et al. "Hypoglycemic effect of ethanolic extract of Musa sapientum on alloxan-induced diabetes mellitus in rats and its relation with antioxidant potential." Journal of herbal pharmacotherapy 5.2 (2005): 7-19. APA.*
https://ginas.ncats.nih.gov/ginas/app/substance/45b74bfb Entry for *Musa sapientum* (Banana) flower extract, accessed Oct. 17, 2016.*
Bhaskar, Jamuna J., Nandini D. Chilkunda, and Paramahans V. Salimath. "Banana (*Musa*sp. var. *elakki bale*) flower and pseudostem: dietary fiber and associated antioxidant capacity." Journal of agricultural and food chemistry 60.1 (2011): 427-432.*

(Continued)

*Primary Examiner* — Nissa Westerberg
(74) *Attorney, Agent, or Firm* — Muncy, Geissler, Olds & Lowe, P.C.

(57) ABSTRACT

The present invention provides a method for treatment of prostatic hyperplasia with banana flower extract. Such banana flower extract can suppress the proliferation of prostate cells and their ability to synthesize dihydrotestosterone. In another aspect, the banana flower extract is also used for ameliorating urinary disturbance. The banana flower extract is a water-soluble extract obtained by sonication and can further be utilized to provide alternatives or supplements for ameliorating symptoms associated with prostatic hyperplasia.

8 Claims, 4 Drawing Sheets

(56) References Cited

OTHER PUBLICATIONS

Wang, Delin, and Keong Tatt Foo. "Staging of benign prostate hyperplasia is helpful in patients with lower urinary tract symptoms suggestive of benign prostate hyperplasia." Annals Academy of Medicine Singapore 39.10 (2010): 798.*

Zhang, Q., et al. "Effects of the polysaccharide fraction of Urtica fissa on castrated rat prostate hyperplasia induced by testosterone propionate." Phytomedicine 15.9 (2008): 722-727.*

* cited by examiner

METHOD FOR TREATMENT OF PROSTATIC HYPERPLASIA AND/OR AMELIORATING URINARY DISTURBANCE WITH BANANA FLOWER EXTRACT

CROSS-REFERENCE TO RELATED APPLICATION

This application claims the priority of Taiwan patent application No. 103132577, filed on Sep. 22, 2014, and Taiwan patent application No. 104128175, filed on Aug. 27, 2015. All disclosure of which is incorporated herein by reference in its entirety

BACKGROUND OF THE INVENTION

1. Field of the Invention

The present invention relates generally to a method of treating prostatic hyperplasia by using banana flower extract, and more particularly, to a method of treating prostatic hyperplasia and/or ameliorating urinary disturbance by using banana stamen extract.

2. The Prior Arts

Banana is one of main economy crop in Taiwan. Bananas are also rich in vitamins and minerals, such as vitamin C, potassium and magnesium. Bananas have the terminal spike inflorescence: male flowers are present in the upper part, female flowers towards the base and the neutral flowers are found in the middle between the male and female flowers. The major difference in three types of flowers is the length of ovaries and stamens. Female flower ovary length is around ⅔ of total flower length, and stamens are degrade; neutral flower ovary length is around ½ of total flower length, and stamens are absent; male flower ovary length is around ⅓ of total flower length, and stamens are well-developed. Actually, rare people know that banana flowers exhibit high nutritional value like banana, and only the female flowers will have fruits, the neutral and male flowers will be removed to be fertilizer, which protects the essential nutrients for fruit growing from excessive consumption. Therefore, only the banana farmers or Taiwan indigenous people put banana flowers into dish. It remains to be studied about banana flowers, especially banana stamens.

Prostate is one of the major organs and an exocrine gland of the male reproductive system in mammals. The function of the prostate is to secrete and store prostatic fluid. For human, the size of a prostate in a healthy male is approximately bigger than a walnut, and the prostate is located at the base of the pelvis, below the bladder, upper end of the urethra, behind the pubic bone and in the front of rectum. About 50 percent of men in their 60 s have an enlarged prostate (benign prostatic hyperplasia, BPH) as they grow older. Enlargement of the prostate gland result from a proliferation of cells in the central region of the prostate, which contributes to symptoms of compressing the urethra caused urinary obstruction, including frequent urination, decreased urinary flow rates, difficulty urinating and interrupted urine flow and post voiding urinary dribbling, and affects the quality of people's lives. Although there is not yet proof an association between prostatic hyperplasia and prostate cancer, but for men's healthy, especially among older men, prostate health maintenance should not be ignored.

The present invention is to provide a method of inhibiting the proliferation of prostate cell and synthesizing dihydrotestosterone by using banana flower extract isolated from banana, a common and abundant fruit in Taiwan. The banana flower extract may be safe and no side effects as health food ingredients and pharmaceutical composition to ameliorating the symptoms caused by prostatic hyperplasia.

SUMMARY OF THE INVENTION

A objective of the present invention is to provide a method of treating a symptom or disorder associated with prostatic hyperplasia, comprising administering an effective amount of a banana flower extract to a subject in need, wherein the symptom or disorder associated with prostatic hyperplasia is an urinary disturbance.

According to an embodiment of the present invention, the banana flower extract reduces at least 40% of the urinary disturbance.

According to an embodiment of the present invention, the banana flower extract inhibits at least 50% of prostate cell proliferation stimulated by testosterone.

According to an embodiment of the present invention, the banana flower extract reduces at least 30% of synthesizing dihydrotestosterone stimulated by testosterone in the prostate cell.

According to an embodiment of the present invention, the urinary disturbance is post voiding urinary dribbling, frequent urination, interrupted urine flow, urgent urination, weak urinary stream, difficulty urinating or increasing the number of nocturia.

According to an embodiment of the present invention, the effective amount is at least 2 mg/mL.

According to an embodiment of the present invention, the prostatic hyperplasia is stage II benign prostatic hyperplasia (BPH).

According to an embodiment of the present invention, the banana flower extract is a banana stamen extract.

Another objective of the present invention is to provide a composition comprising: a core comprising a banana flower extract; and a layer of natural polymeric material enveloping the core.

According to an embodiment of the present invention, the banana flower extract, wherein the banana flower extract is a banana stamen extract.

According to an embodiment of the present invention, the core further comprises an additive or pharmacological acceptable excipient.

According to an embodiment of the present invention, the composition is in the form of tablet or powder; and filled in a capsule.

According to an embodiment of the present invention, the composition is used as a food or pharmaceutical composition.

According to an embodiment of the present invention, the additive is citric acid, taurine, vitamins, pantothenic acid or nicotinic acid.

Another objective of the present invention is to provide an aqueous composition comprising: a banana flower extract; and a solubilizing agent; wherein the banana flower extract is a banana stamen extract.

The present invention provides a method of treating a symptom or disorder associated with prostatic hyperplasia by using the banana flower extract; that can inhibit prostate cell proliferation, more specially, can inhibit the ability of synthesizing dihydrotestosterone stimulated by testosterone in the prostate cell to ameliorate urinary disturbance caused by prostatic hyperplasia. Furthermore, the banana flower extract can be as a new ingredient in the food composition or pharmaceutical composition, which can be in the form of beverage, capsule, tablet or powder.

BRIEF DESCRIPTION OF THE DRAWINGS

The present invention will be apparent to those skilled in the art by reading the following detailed description of a preferred embodiment thereof, with reference to the attached drawings, in which:

FIG. 4A is an ultrasound image of the prostate of a patient suffering from prostatic hyperplasia before administrating the banana flower extract; FIG. 4B is an ultrasound image of the prostate of a patient suffering from prostatic hyperplasia after administrating the banana flower extract for 1 month.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Definition

The "effective dosage" or "effective amount" represents the dosage of the banana flower extract that can inhibit prostate cell proliferation and the ability of synthesizing dihydrotestosterone stimulated by testosterone in the prostate cell. The appropriate effective amount may vary depending on the organism or individual treated but can be determined experimentally using various techniques, including a dose escalation study.

As used herein, the data provided represent experimental values that can vary within a range of ±20%, preferably within ±10%, and most preferably within ±5%.

The present invention prepares the banana flower extract, and treats the prostate cells with testosterone, the banana flower extract of the present invention and the commercial androgen receptor modulators for in vitro experiment to evaluate the effects of the banana flower extract of the present invention on prostate cell proliferation and dihydrotestosterone synthesis. Moreover, the present invention also provides within-subject comparison in a score chart and ultrasound images of the prostate to evaluate the effects of the banana flower extract of the present invention on ameliorating prostatic hyperplasia for in vivo experiment.

Example 1

Preparation of the Banana Flower Extract

Figure 1:
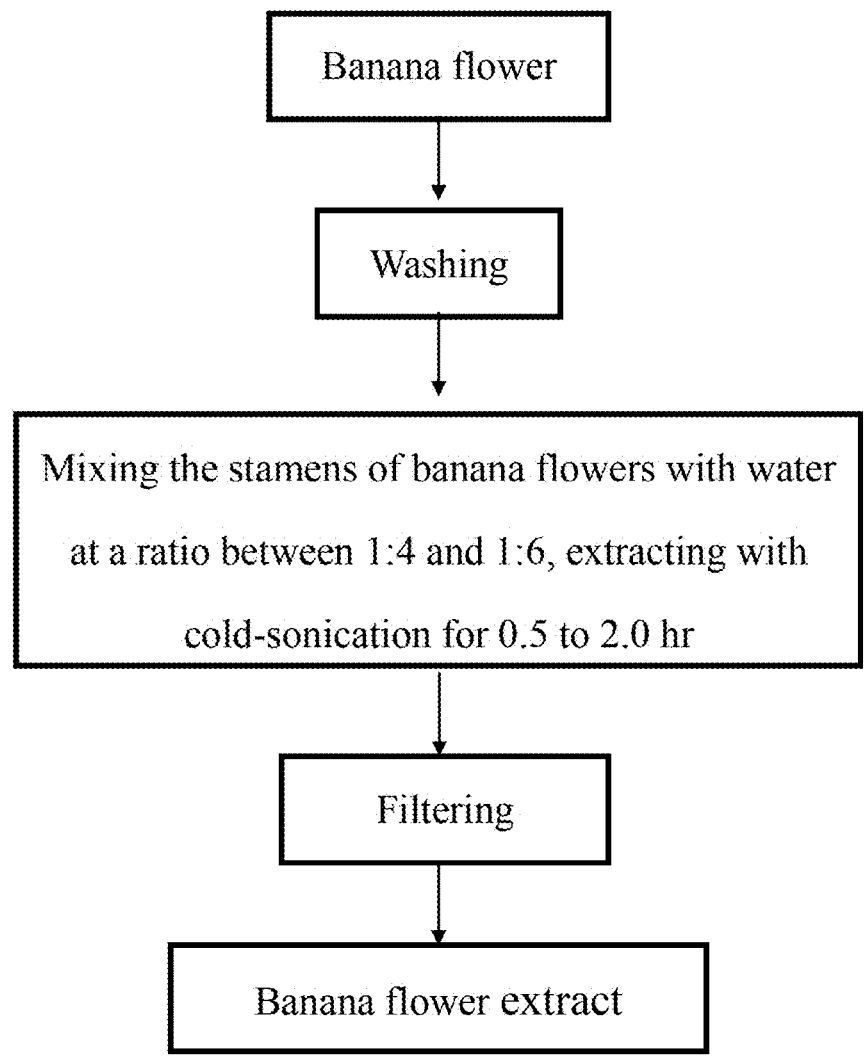
FIG. 1 shows a flowchart for isolation of the banana flower extract of the present invention.

FIG. 1 shows a flowchart for isolation of the banana flower extract of the present invention. The banana flowers are used in the present invention including but not limiting from the flowers of *Musa paradisiacal, Musa sapientum L., Musa* spp. *AAB Silk, Musa* spp. *ABB Bluggoe, Musa* spp. *AAA Robusta, Musa* spp. *AAB Bluggoe,* etc. *Musa paradisiacal* is preferably. Firstly, the stamens of banana flowers are harvested by labor or machine, and cleaned with water. The stamens of banana flowers are mixed with water at a ratio between 1:4 and 1:6, extracted with cold-sonication for 0.5 to 2.0 hr to obtain a crude banana flower extract. Finally, the crude banana flower extract is centrifuged and filtered through a 300 mesh screen to obtain the banana flower extract of the present invention.

Example 2

Effect of the Banana Flower Extract on Inhibiting Prostate Cell Proliferation Stimulated by Testosterone In one embodiment, LNCap human prostate cancer cell lines (BCRC 60088) purchased from Bioresource Collection and Research Center (BCRC) are used. $2 \times 10^4$ LNCap cells/well are placed in the 96-well plate and cultured for 24 hr. LNCap cells treated with testosterone and various concentrations (0.5 mg/mL and 2.0 mg/mL) of the banana flower extract, and co-cultured for 3 days. LNCap cells are treated with the banana flower extract without testosterone as negative control, and LNCap cells are treated with testosterone without the banana flower extract as vehicle control. The survival rate of LNCap cells is evaluated using the MTT assay, LNCap cells are treated with 1 mg/mL MTT (3-[4,5-dimethyl thiazol-2-yl]-2,5diphenyl tetrazolium bromide) for 2 hr, and dimethyl sulfoxide (DMSO) is added to dissolve blue formazan crystals. An absorbance is measured using a reader at the wavelength of 570 nm.

Figure 2:
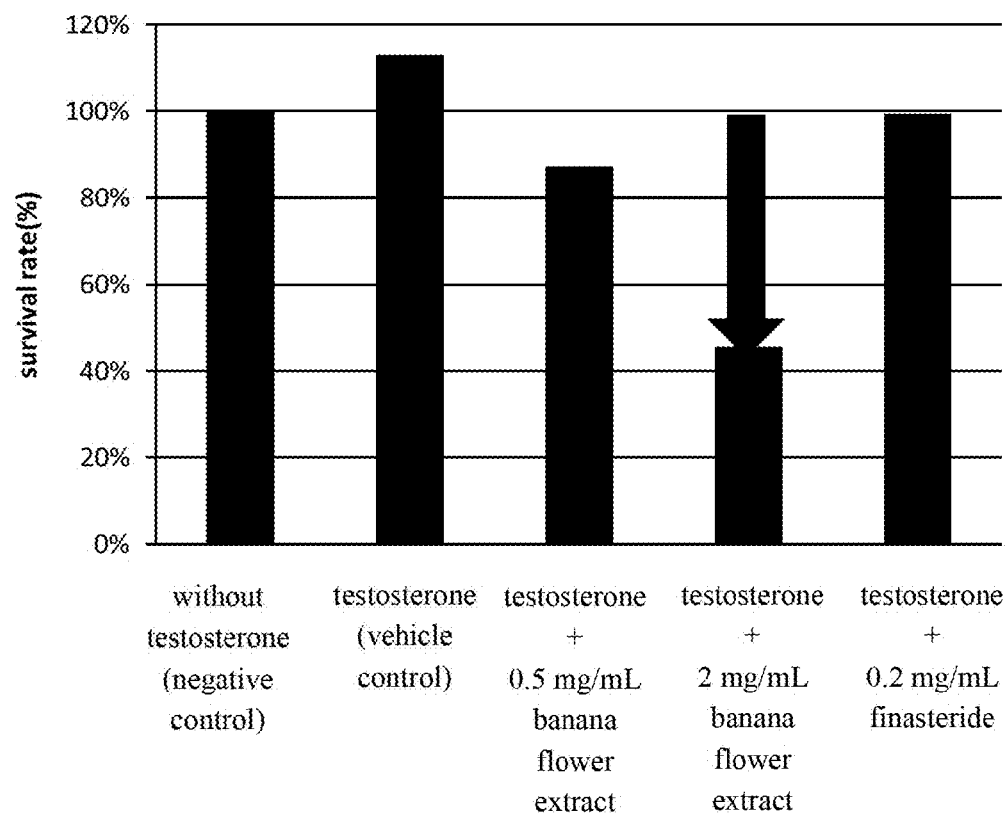
FIG. 2 shows the effect of the banana flower extract of the present invention on inhibiting prostate cell proliferation stimulated by testosterone.

As shown in FIG. 2, the survival rate of LNcap cells without testosterone treatment is 100%; as treating with testosterone, the survival rate of LNcap cells is about 110%, which shows that testosterone stimulates LNcap cell proliferation. As treating with testosterone and the banana flower extract (0.5 mg/mL), the survival rate of LNcap cells is a decrease of about 90%; As treating with testosterone and the banana flower extract (2.0 mg/mL), the survival rate of LNcap cells is a decrease of about 50%. Regarding the co-treatment of testosterone and 0.2 mg/mL finasteride, finasteride may slightly inhibit LNcap cell proliferation stimulated by testosterone. Therefore, the banana flower extract can not only inhibit the prostate cell proliferation but also can exhibit a better effect than a commercial androgen receptor modulator, such as finasteride, on inhibiting the prostate cell proliferation.

Example 3

Effect of the Banana Flower Extract on Synthesizing Dihydrotestosterone Stimulated by Testosterone in the Prostate Cell $1 \times 10^5$ LNCap cells/well are cultured with RPMI 1640 containing 10% FBS and 1% sodium pyruvate in 9-cm culture plate for 36 hr. LNCap cells are treated with phosphate-buffered saline, 2 mg/mL the banana flower extract of the present invention, 20 μg/mL finasteride, respectively. And all LNCap cells are stimulated by 10 μg/mL testosterone.

Cell lysis is processed prior to analysis of dihydrotestosterone level: LNCap cells are dispersed with typsin and centrifuged to collect the suspension cells, the suspension cells are washed with cold PBS, and the suspension cells are resuspended in PBS(1×) and sonicated 4 times; or LNCap cells are frozen at −20° C. or lower, and stirred frequently until thawed for 3 times to destroy cells. The destroyed cells are centrifuged at 150× g at 2-8° C. for 10 min to remove the cell debris. Finally, dihydrotestosterone ELISA Kit (Uscn Life science Inc.) is used to detect dihydrotestosterone level.

Figure 3:
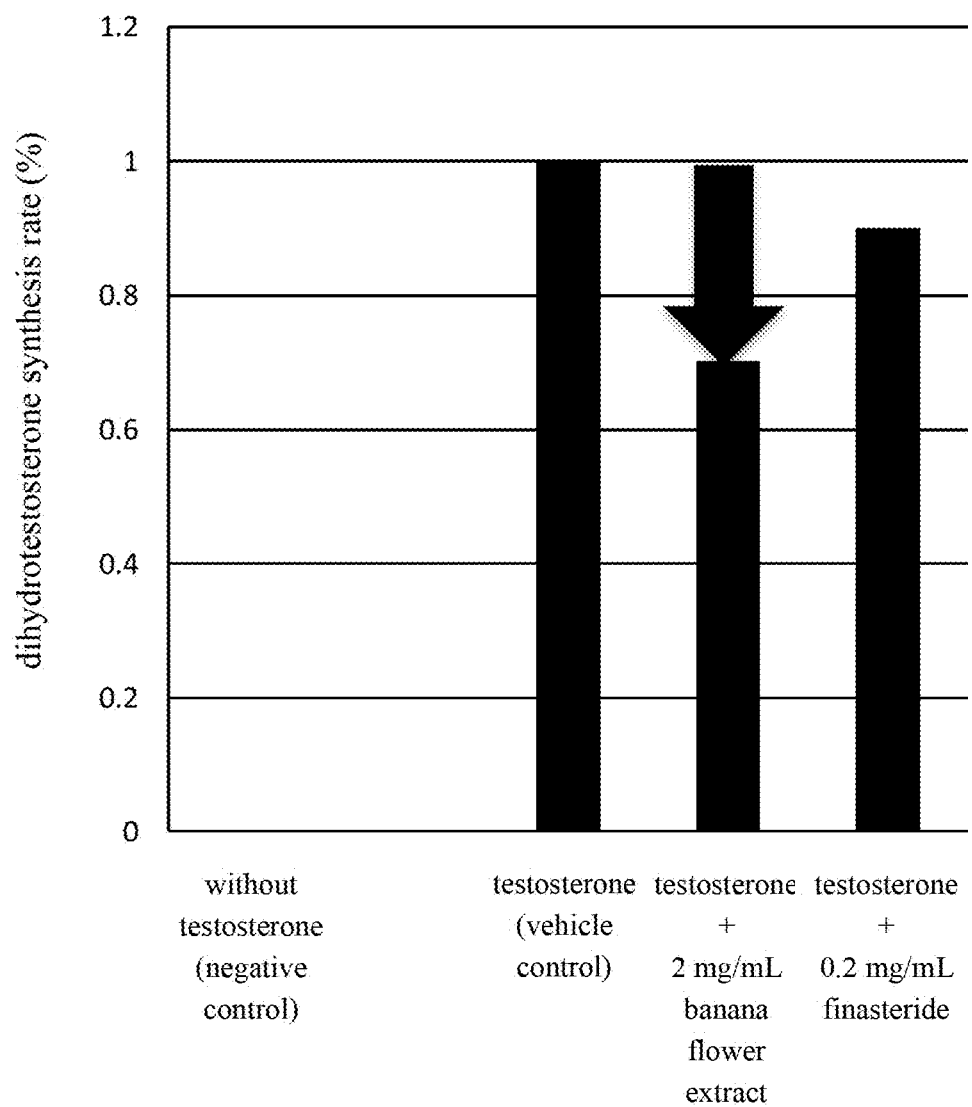
FIG. 3 shows the effect of the banana flower extract of the present invention on inhibiting dihydrotestosterone level stimulated by testosterone in the prostate cell. LNCap cells treated with the banana flower extract without testosterone is negative control, which shows that the background dihydrotestosterone level detected is 0%.

LNCap cells are treated with the banana flower extract of the present invention and testosterone as above-mentioned method, LNCap cells treated with the banana flower extract without testosterone as negative control, and LNCap cells treated with testosterone without the banana flower extract as vehicle control, are detected dihydrotestosterone level. As shown in FIG. 3, the dihydrotestosterone synthesis rate of LNCap cells without testosterone is 0%; as treating with testosterone, the dihydrotestosterone synthesis rate of LNCap cells is 100%. As co-treating with testosterone and the banana flower extract (2 mg/mL), the dihydrotestosterone synthesis rate of LNcap cells is decreased about 30%. Regarding the co-treatment of testosterone and 0.2 mg/mL finasteride, finasteride may only reduce 10% of the dihydrotestosterone synthesis rate. The results show that the banana flower extract can exhibit a better effect than a commercial androgen receptor modulator, such as finasteride, on inhibiting dihydrotestosterone synthesis.

Example 4

Effect of the Banana Flower Extract on Ameliorating Symptoms Associated with Prostatic Hyperplasia To validate the banana flower extract of the present invention having the ability of ameliorating symptoms associated with prostatic hyperplasia, preparing a tablet containing 1 g the banana flower extract of the present invention and at least a pharmacological acceptable excipient. The banana flower extract of the present invention can be made powered by a well-known method, such as a supercritical fluid high-pressure spray process. Participants in the embodiment are 8 patients aged 70 to 80 suffering from prostatic hyperplasia, they take a tablet containing 1 g the banana flower extract of the present invention once a day for one month. Among all participants, there are 5 participants compared in within-subject comparison in the International Prostate Symptom Score (IPSS) to evaluate the effects of before and after the banana flower extract administration on ameliorating prostatic hyperplasia (participants labeled as A, B, C, D and E). Severity of symptom is on a scale from 0 to 3, 0 represents no symptom; 3 represents most severe. The results as follows:

TABLE 1

| | A | B | C | D | E |
|---|---|---|---|---|---|
| Before administration | | | | | |
| post voiding urinary dribbling | 2 | 1 | 1 | 3 | 0 |
| frequent urination | 1 | 1 | 1 | 3 | 0 |
| interrupted urine flow | 1 | 1 | 1 | 3 | 0 |
| urgent urination | 0 | 0 | 0 | 0 | 0 |
| weak urinary stream | 1 | 0 | 1 | 3 | 0 |
| difficulty urinating | 1 | 0 | 0 | 2 | 0 |
| increasing the number of nocturia | 1 | 2 | 1 | 1 | 1 |
| Total score before administration | 7 | 5 | 5 | 15 | 1 |
| Administration for one month | | | | | |
| post voiding urinary dribbling | 1 | 1 | 1 | 1 | 0 |
| frequent urination | 1 | 1 | 1 | 1 | 1 |
| interrupted urine flow | 1 | 1 | 1 | 0 | 0 |
| urgent urination | 0 | 0 | 0 | 0 | 0 |
| weak urinary stream | 1 | 0 | 1 | 0 | 0 |
| difficulty urinating | 1 | 0 | 0 | 1 | 0 |
| increasing the number of nocturia | 1 | 2 | 1 | 1 | 1 |
| Total score after administration | 6 | 5 | 5 | 4 | 2 |
| Determining the Effects (Total score before administration > Total score after administration) | effective | ineffective | ineffective | effective | ineffective |

As shown in Table 1, after administration the tablet containing 1 g the banana flower extract for one month, symptoms associated with prostatic hyperplasia have improve, the improving rate is 40% (the tablet is effective in 2 out of 5 participants). Moreover, the banana flower extract has dose-dependent efficacy, for example, the increased dose of the banana flower extract (e.g. up to 1.5 g or 2 g) can raise the feelings of ameliorating symptoms associated with prostatic hyperplasia (e.g. patient has a strong urine flow and bladder).

Figure 4A:
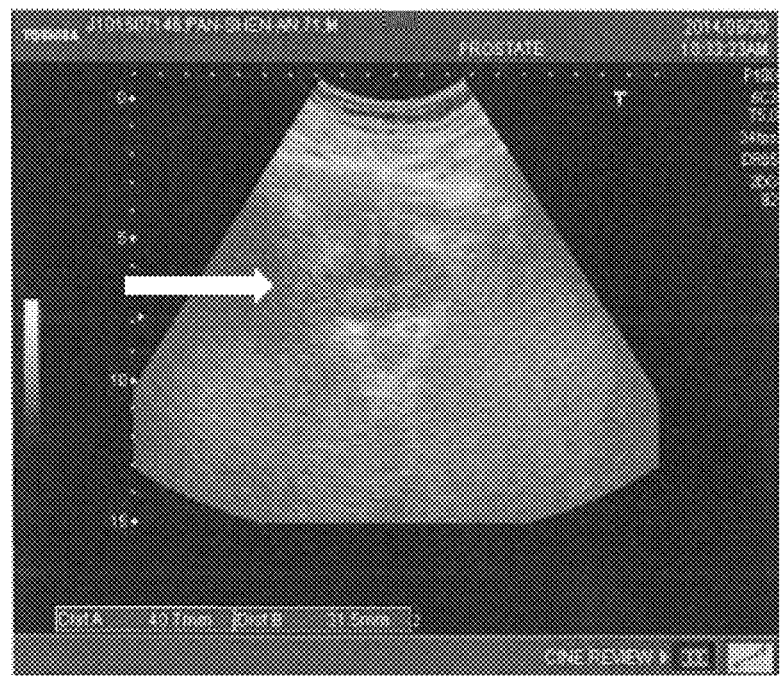
FIGS. 4A and 4B show the effect of the banana flower extract of the present invention on ameliorating prostatic hyperplasia to synthesize dihydrotestosterone stimulated by testosterone in the prostate cell.
Figure 4B:
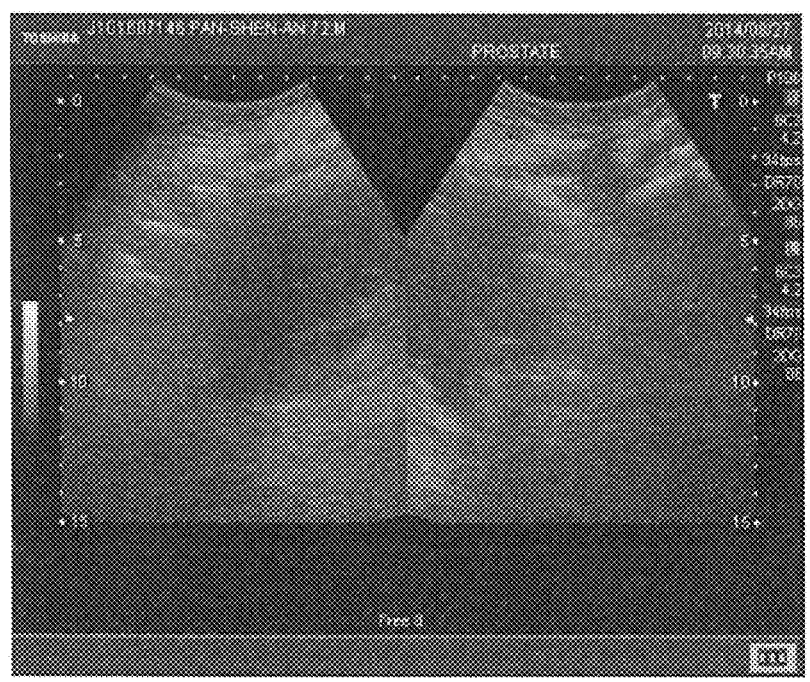

On the other hand, administrating the tablet containing 1 g the banana flower extract for one month can improve stage II benign prostatic hyperplasia (BPH) to stage I BPH, as shown in FIGS. 4A and 4B. In FIG. 4A, white arrow indicates stage II BPH. After administration the tablet containing 1 g the banana flower extract for one month, the size and shape of prostate enlargement are significantly decreased, as shown in FIG. 4B, the position corresponding to stage II BPH indicated by white arrow in FIG. 4A has been improved to stage I BPH.

Thus, the banana flower extract of the present invention can be used to prepare a composition for treating prostatic hyperplasia and/or ameliorating urinary disturbance caused by prostatic hyperplasia, the composition can be a substitute or supplement for ameliorating symptoms associated with prostatic hyperplasia. For example, the composition can be a pharmaceutical composition containing an effective amount of the banana flower extract of the present invention for ameliorating symptoms associated with prostatic hyperplasia, and the pharmaceutical composition can further comprise a pharmacological acceptable excipient. Additionally, the banana flower extract can be used to prepare a food composition for ameliorating symptoms associated with prostatic hyperplasia, the food composition can further comprise an additive, the additive is a health food ingredient, material or composition thereof. The health food ingredient can be citric acid, taurine, vitamins, pantothenic acid, nicotinic acid or other ingredients beneficial to human health, etc. The material is fruit, vegetable, meat or other food material, but not limited thereto.

In summary, the present invention provides a method of treating a symptom or disorder associated with prostatic hyperplasia by the banana flower extract, which can effectively inhibit prostate cell proliferation and dihydrotestosterone synthesis stimulated by testosterone, therefore, symptoms associated with prostatic hyperplasia including prostate enlargement, frequent urination, difficulty urinating can be improved. The banana flower extract of the present invention may not cause side effect of a conventional artificial inhibitor, it can be used to prepare a pharmaceutical composition. Therefore, the banana flower extract of the present invention is dissolve and has a good thermal stability; it can be given people in variety of formulated functional foods and beverages.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method of treating a symptom or disorder associated with prostatic hyperplasia, comprising administering an effective amount of a banana flower water extract to a subject in need thereof, wherein the extract is extracted solely from stamens of banana flowers mixed with water using cold-sonication, and wherein the symptom or disorder associated with prostatic hyperplasia is urinary disturbance.

2. The method according to claim 1, wherein the banana flower water extract reduces at least 40% of the urinary disturbance.

3. The method according to claim 1, wherein the banana flower water extract inhibits at least 50% of a prostate cell proliferation stimulated by testosterone.

4. The method according to claim 1, wherein, the banana flower water extract reduces at least 30% of synthesizing dihydrotestosterone stimulated by testosterone in a prostate cell.

5. The method according to claim 1, wherein the urinary disturbance is post voiding urinary dribbling, frequent urination, interrupted urine flow, urgent urination, weak urinary stream, difficulty urinating or increasing the number of nocturia.

6. The method according to claim 1, wherein the effective amount is at least 2 mg/mL.

7. The method according to claim 1, wherein the prostatic hyperplasia is stage II benign prostatic hyperplasia (BPH).

8. The method according to claim 1, wherein the stamens of banana flowers and water are mixed at a ratio between 1:4 and 1:6.

* * * * *